US010222956B2

(12) United States Patent
Gopinath et al.

(10) Patent No.: US 10,222,956 B2
(45) Date of Patent: Mar. 5, 2019

(54) INTRAVASCULAR IMAGING USER INTERFACE SYSTEMS AND METHODS

(71) Applicant: LightLab Imaging, Inc., Westford, MA (US)

(72) Inventors: Ajay Gopinath, Bedford, MA (US); Subhan Khan, Weston, MA (US); Denis Dion, Dracut, MA (US)

(73) Assignee: LIGHTLAB IMAGING, INC., Westford, MA (US)

( * ) Notice: Subject to any disclaimer, the term of this patent is extended or adjusted under 35 U.S.C. 154(b) by 68 days.

(21) Appl. No.: 14/975,671

(22) Filed: Dec. 18, 2015

(65) Prior Publication Data

US 2017/0103520 A1 Apr. 13, 2017

Related U.S. Application Data

(60) Provisional application No. 62/241,056, filed on Oct. 13, 2015.

(51) Int. Cl.
*G06F 3/0484* (2013.01)
*A61B 5/00* (2006.01)
(Continued)

(52) U.S. Cl.
CPC ........ *G06F 3/04842* (2013.01); *A61B 5/0066* (2013.01); *A61B 5/0084* (2013.01);
(Continued)

(58) Field of Classification Search
CPC .... A61B 2034/2065; A61B 2090/3735; A61B 2090/3782; A61B 5/0066; A61B 5/0084;
(Continued)

(56) References Cited

U.S. PATENT DOCUMENTS

| 4,548,473 A | 10/1985 | Lo et al. |
|---|---|---|
| 5,054,492 A | 10/1991 | Scribner et al. |

(Continued)

FOREIGN PATENT DOCUMENTS

| EP | 2062526 | 5/2009 |
|---|---|---|
| JP | 63-127201 | 5/1988 |

(Continued)

OTHER PUBLICATIONS

Briguori et al., "Intravascular ultrasound criteria for the assessment of the functional significance of intermediate coronary artery stenoses and comparison with fractional flow reserve," Am J. Cardiol 87:136-141, 2001.

(Continued)

*Primary Examiner* — Manuchehr Rahmjoo
(74) *Attorney, Agent, or Firm* — K&L Gates LLP

(57) ABSTRACT

In part, the disclosure relates to intravascular data collections and generation of representations thereof include one or more view of regions associated with side branches or arteries such as a carina or bifurcation. In one embodiment, accessing a set of intravascular data stored in machine readable memory; performing side branch detection with regard to the intravascular data to identify one or more side branches; and identifying a plurality of frames for the one or more side branches is performed. An automatic viewing angle that is toggleable is used in one embodiment.

20 Claims, 11 Drawing Sheets

(51) Int. Cl.
   *A61B 5/02* (2006.01)
   *G06T 19/00* (2011.01)
(52) U.S. Cl.
   CPC .......... *A61B 5/02007* (2013.01); *A61B 5/489* (2013.01); *A61B 5/74* (2013.01); *G06T 19/00* (2013.01); *G06T 2210/41* (2013.01); *G06T 2219/008* (2013.01)
(58) Field of Classification Search
   CPC .................. A61B 5/1076; A61B 5/489; G06T 2207/10101; G06T 2207/30101; G06T 7/11; G06T 7/174; G06T 7/194
   USPC ........................................................ 382/100
   See application file for complete search history.

(56) References Cited

U.S. PATENT DOCUMENTS

| | | |
|---|---|---|
| 5,321,501 A | 6/1994 | Swanson et al. |
| 5,459,570 A | 10/1995 | Swanson et al. |
| 5,465,147 A | 11/1995 | Swanson |
| 5,477,858 A | 12/1995 | Norris et al. |
| 5,488,674 A | 1/1996 | Burt et al. |
| 5,509,093 A | 4/1996 | Miller et al. |
| 5,518,810 A | 5/1996 | Nishihara et al. |
| 5,531,227 A | 7/1996 | Schneider |
| 5,586,201 A | 12/1996 | Whiting et al. |
| 5,619,368 A | 4/1997 | Swanson |
| 5,632,767 A | 5/1997 | Sinofsky |
| 5,643,253 A | 7/1997 | Baxter et al. |
| 5,662,109 A | 9/1997 | Hutson |
| 5,715,827 A | 2/1998 | Corl et al. |
| 5,748,598 A | 5/1998 | Swanson et al. |
| 5,771,895 A | 6/1998 | Slager |
| 5,784,352 A | 7/1998 | Swanson et al. |
| 5,797,849 A | 8/1998 | Vesely et al. |
| 5,822,391 A | 10/1998 | Whiting |
| 5,908,415 A | 6/1999 | Sinofsky |
| 5,947,959 A | 9/1999 | Sinofsky |
| 5,956,355 A | 9/1999 | Swanson et al. |
| 5,989,189 A | 11/1999 | LeBlanc et al. |
| 6,111,645 A | 8/2000 | Tearney et al. |
| 6,134,003 A | 10/2000 | Tearney et al. |
| 6,148,095 A | 11/2000 | Prause et al. |
| 6,160,826 A | 12/2000 | Swanson et al. |
| 6,191,862 B1 | 2/2001 | Swanson et al. |
| 6,195,445 B1 | 2/2001 | Jolly et al. |
| 6,208,883 B1 | 3/2001 | Holupka et al. |
| 6,270,492 B1 | 8/2001 | Sinofsky |
| 6,282,011 B1 | 8/2001 | Tearney et al. |
| 6,302,875 B1 | 10/2001 | Makower et al. |
| 6,348,960 B1 | 2/2002 | Etori et al. |
| 6,381,350 B1 | 4/2002 | Klingensmith et al. |
| 6,385,332 B1 | 5/2002 | Zahalka et al. |
| 6,421,164 B2 | 7/2002 | Tearney et al. |
| 6,445,939 B1 | 9/2002 | Swanson et al. |
| 6,471,656 B1 | 10/2002 | Shalman et al. |
| 6,485,413 B1 | 11/2002 | Boppart et al. |
| 6,501,551 B1 | 12/2002 | Tearney et al. |
| 6,552,796 B2 | 4/2003 | Magnin et al. |
| 6,564,087 B1 | 5/2003 | Pitris et al. |
| 6,565,514 B2 | 5/2003 | Svanerudh et al. |
| 6,570,659 B2 | 5/2003 | Schmitt |
| 6,585,660 B2 | 7/2003 | Dorando et al. |
| 6,692,824 B2 | 2/2004 | Benz et al. |
| 6,697,667 B1 | 2/2004 | Lee et al. |
| 6,706,004 B2 | 3/2004 | Tearney et al. |
| 6,716,178 B1 | 4/2004 | Kilpatrick et al. |
| 6,718,089 B2 | 4/2004 | James et al. |
| 6,728,566 B1 | 4/2004 | Subramanyan et al. |
| 6,731,973 B2 | 5/2004 | Voith |
| 6,760,112 B2 | 7/2004 | Reed et al. |
| 6,785,409 B1 | 8/2004 | Suri |
| 6,868,736 B2 | 3/2005 | Sawatari et al. |
| 6,879,851 B2 | 4/2005 | McNamara et al. |
| 6,891,984 B2 | 5/2005 | Petersen et al. |
| 6,932,809 B2 | 8/2005 | Sinofsky |
| 6,937,696 B1 | 8/2005 | Mostafavi |
| 6,942,657 B2 | 9/2005 | Sinofsky et al. |
| 6,947,040 B2 | 9/2005 | Tek et al. |
| 6,973,202 B2 | 12/2005 | Mostafavi |
| 6,974,557 B1 | 12/2005 | Webler et al. |
| 7,068,831 B2 | 6/2006 | Florent et al. |
| 7,134,994 B2 | 11/2006 | Alpert et al. |
| 7,191,100 B2 | 3/2007 | Mostafavi |
| 7,208,333 B2 | 4/2007 | Flanders et al. |
| 7,231,243 B2 | 6/2007 | Tearney et al. |
| 7,241,286 B2 | 7/2007 | Atlas |
| 7,298,478 B2 | 11/2007 | Gilbert et al. |
| 7,301,644 B2 | 11/2007 | Knighton et al. |
| 7,321,677 B2 | 1/2008 | Evron et al. |
| 7,329,223 B1 | 2/2008 | Ainsworth et al. |
| 7,355,699 B2 | 4/2008 | Gilbert et al. |
| 7,359,554 B2 | 4/2008 | Klingensmith et al. |
| 7,397,935 B2 | 7/2008 | Kimmel et al. |
| 7,408,648 B2 | 8/2008 | Kleen et al. |
| 7,412,141 B2 | 8/2008 | Gowda et al. |
| 7,414,779 B2 | 8/2008 | Huber et al. |
| 7,415,049 B2 | 8/2008 | Flanders et al. |
| 7,450,241 B2 | 11/2008 | Zuluaga |
| RE40,608 E | 12/2008 | Glover et al. |
| 7,492,522 B2 | 2/2009 | Gilbert et al. |
| 7,532,920 B1 | 5/2009 | Ainsworth et al. |
| 7,576,861 B2 | 8/2009 | Gilbert et al. |
| 7,593,559 B2 | 9/2009 | Toth et al. |
| 7,610,081 B2 | 10/2009 | Redel |
| 7,619,646 B2 | 11/2009 | Freifeld et al. |
| 7,625,366 B2 | 12/2009 | Atlas |
| 7,627,156 B2 | 12/2009 | Margolis et al. |
| 7,650,179 B2 | 1/2010 | Redel et al. |
| 7,679,754 B2 | 3/2010 | Zuluaga |
| 7,697,972 B2 | 4/2010 | Verard et al. |
| 7,706,585 B2 | 4/2010 | Kleen |
| 7,711,413 B2 | 5/2010 | Feldman et al. |
| 7,729,746 B2 | 6/2010 | Redel et al. |
| 7,733,497 B2 | 6/2010 | Yun et al. |
| 7,742,797 B2 | 6/2010 | Redel et al. |
| 7,783,337 B2 | 8/2010 | Feldman et al. |
| 7,783,338 B2 | 8/2010 | Ainsworth et al. |
| 7,785,286 B2 | 8/2010 | Magnin et al. |
| 7,792,342 B2 | 9/2010 | Barbu et al. |
| 7,801,343 B2 | 9/2010 | Unal et al. |
| 7,813,609 B2 | 10/2010 | Petersen et al. |
| 7,831,078 B2 | 11/2010 | Unal et al. |
| 7,843,976 B2 | 11/2010 | Cable et al. |
| 7,848,791 B2 | 12/2010 | Schmitt et al. |
| 7,853,316 B2 | 12/2010 | Milner et al. |
| 7,869,663 B2 | 1/2011 | Buckland et al. |
| 7,872,759 B2 | 1/2011 | Tearney et al. |
| 7,916,387 B2 | 3/2011 | Schmitt |
| 7,918,793 B2 | 4/2011 | Altmann et al. |
| 7,925,327 B2 | 4/2011 | Weese |
| 7,930,014 B2 | 4/2011 | Huennekens et al. |
| 7,935,060 B2 | 5/2011 | Schmitt et al. |
| 7,967,743 B2 | 6/2011 | Ishihara |
| 7,988,633 B2 | 8/2011 | Hossack et al. |
| 7,991,105 B2 | 8/2011 | Mielekamp et al. |
| 8,029,447 B2 | 10/2011 | Kanz et al. |
| 8,116,605 B2 | 2/2012 | Petersen et al. |
| 8,206,374 B2 | 6/2012 | Duane et al. |
| 8,206,377 B2 | 6/2012 | Petroff |
| 8,208,995 B2 | 6/2012 | Tearney et al. |
| 8,223,143 B2 | 7/2012 | Dastmalchi et al. |
| 8,259,303 B2 | 9/2012 | Johnson et al. |
| 8,290,228 B2 | 10/2012 | Cohen et al. |
| 8,298,147 B2 | 10/2012 | Huennekens et al. |
| 8,315,282 B2 | 11/2012 | Huber et al. |
| 8,325,419 B2 | 12/2012 | Schmitt |
| 8,351,665 B2 | 1/2013 | Tearney et al. |
| 8,358,461 B2 | 1/2013 | Huber et al. |
| 8,423,121 B2 | 4/2013 | Wang et al. |
| 8,449,468 B2 | 5/2013 | Petersen et al. |
| 8,457,375 B2 | 6/2013 | Rieber et al. |
| 8,457,440 B1 | 6/2013 | Johnson |

(56) References Cited

U.S. PATENT DOCUMENTS

| | | |
|---|---|---|
| 8,463,007 B2 | 6/2013 | Steinberg et al. |
| 8,478,384 B2 | 7/2013 | Schmitt et al. |
| 8,478,387 B2 | 7/2013 | Xu |
| 8,503,844 B2 | 8/2013 | Petersen et al. |
| 8,542,900 B2 | 9/2013 | Tolkowsky et al. |
| 8,556,820 B2 | 10/2013 | Alpert et al. |
| 8,562,537 B2 | 10/2013 | Alpert et al. |
| 8,571,639 B2 | 10/2013 | Mostafavi |
| 8,581,643 B1 | 11/2013 | Schmitt |
| 8,582,109 B1 | 11/2013 | Schmitt |
| 8,582,619 B2 | 11/2013 | Adler |
| 8,582,934 B2 | 11/2013 | Adler et al. |
| 8,670,603 B2 | 3/2014 | Tolkowsky et al. |
| 8,687,201 B2 | 4/2014 | Adler |
| 8,693,756 B2 | 4/2014 | Tolkowsky et al. |
| 8,700,130 B2 | 4/2014 | Iddan et al. |
| 8,781,193 B2 | 7/2014 | Steinberg et al. |
| 8,786,336 B1 | 7/2014 | Schmitt |
| 8,831,321 B1* | 9/2014 | Elbasiony ............ A61B 5/0066 382/131 |
| 8,855,744 B2 | 10/2014 | Tolkowsky et al. |
| 8,909,323 B2 | 12/2014 | Baumgart |
| 8,913,084 B2 | 12/2014 | Chen et al. |
| 8,948,228 B2 | 2/2015 | Adler |
| 8,953,911 B1 | 2/2015 | Xu et al. |
| 8,983,580 B2 | 3/2015 | Boppart et al. |
| 9,069,396 B2 | 6/2015 | Adler et al. |
| 9,173,591 B2 | 11/2015 | Elbasiony |
| 9,308,052 B2 | 4/2016 | Tolkowsky et al. |
| 9,351,698 B2 | 5/2016 | Dascal et al. |
| 9,404,731 B2 | 8/2016 | Adler et al. |
| 9,435,956 B1 | 9/2016 | Xu et al. |
| 9,488,464 B1 | 11/2016 | Schmitt |
| 9,629,571 B2 | 4/2017 | Tolkowsky et al. |
| 2002/0077591 A1* | 6/2002 | Happ ....................... A61F 2/958 604/96.01 |
| 2002/0115931 A1 | 8/2002 | Strauss et al. |
| 2002/0161351 A1 | 10/2002 | Samson et al. |
| 2004/0006277 A1 | 1/2004 | Langenhove et al. |
| 2005/0043614 A1 | 2/2005 | Huizenga et al. |
| 2005/0201662 A1 | 9/2005 | Petersen et al. |
| 2005/0238067 A1 | 10/2005 | Choi |
| 2005/0249391 A1 | 11/2005 | Kimmel et al. |
| 2006/0095065 A1 | 5/2006 | Tanimura et al. |
| 2006/0135870 A1 | 6/2006 | Webler |
| 2006/0165270 A1 | 7/2006 | Borgert et al. |
| 2006/0187537 A1 | 8/2006 | Huber et al. |
| 2006/0203859 A1 | 9/2006 | Cable et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2007/0024617 A1 | 2/2007 | Poole |
| 2007/0060822 A1 | 3/2007 | Alpert et al. |
| 2007/0066890 A1 | 3/2007 | Maschke |
| 2007/0115481 A1 | 5/2007 | Toth et al. |
| 2007/0123771 A1 | 5/2007 | Redel et al. |
| 2007/0135803 A1 | 6/2007 | Belson |
| 2007/0165916 A1 | 7/2007 | Cloutier et al. |
| 2007/0167710 A1 | 7/2007 | Unal et al. |
| 2007/0232933 A1 | 10/2007 | Gille et al. |
| 2007/0260198 A1 | 11/2007 | Atlas |
| 2007/0293932 A1 | 12/2007 | Zilla et al. |
| 2008/0100612 A1 | 5/2008 | Dastmalchi et al. |
| 2008/0161696 A1 | 7/2008 | Schmitt et al. |
| 2008/0165366 A1 | 7/2008 | Schmitt et al. |
| 2008/0221439 A1 | 9/2008 | Iddan et al. |
| 2008/0221440 A1 | 9/2008 | Iddan et al. |
| 2008/0221442 A1 | 9/2008 | Tolkowsky et al. |
| 2008/0228086 A1 | 9/2008 | Ilegbusi et al. |
| 2008/0281205 A1 | 11/2008 | Naghavi et al. |
| 2009/0027051 A1 | 1/2009 | Stuber et al. |
| 2009/0174931 A1 | 7/2009 | Huber et al. |
| 2009/0204134 A1 | 8/2009 | Kassab |
| 2009/0306520 A1 | 12/2009 | Schmitt et al. |
| 2010/0076320 A1 | 3/2010 | Petersen et al. |
| 2010/0094127 A1 | 4/2010 | Xu |
| 2010/0157041 A1 | 6/2010 | Klaiman et al. |
| 2010/0160764 A1 | 6/2010 | Steinberg et al. |
| 2010/0160773 A1 | 6/2010 | Cohen et al. |
| 2010/0161023 A1 | 6/2010 | Cohen et al. |
| 2010/0172556 A1 | 7/2010 | Cohen et al. |
| 2010/0191102 A1 | 7/2010 | Steinberg et al. |
| 2010/0222671 A1 | 9/2010 | Cohen et al. |
| 2010/0228076 A1 | 9/2010 | Blank |
| 2010/0253949 A1 | 10/2010 | Adler et al. |
| 2011/0007315 A1 | 1/2011 | Petersen et al. |
| 2011/0071404 A1 | 3/2011 | Schmitt et al. |
| 2011/0071405 A1 | 3/2011 | Judell et al. |
| 2011/0101207 A1 | 5/2011 | Schmitt |
| 2011/0151980 A1 | 6/2011 | Petroff |
| 2011/0157686 A1 | 6/2011 | Huber et al. |
| 2011/0172511 A1 | 7/2011 | Schmitt et al. |
| 2011/0178413 A1 | 7/2011 | Schmitt et al. |
| 2011/0190586 A1 | 8/2011 | Kemp |
| 2011/0216325 A1 | 9/2011 | Schmitt |
| 2011/0228280 A1 | 9/2011 | Schmitt et al. |
| 2011/0230758 A1 | 9/2011 | Eichler |
| 2011/0257545 A1 | 10/2011 | Sun |
| 2011/0319752 A1 | 12/2011 | Steinberg et al. |
| 2012/0004529 A1 | 1/2012 | Tolkowsky et al. |
| 2012/0029339 A1 | 2/2012 | Cohen et al. |
| 2012/0057157 A1 | 3/2012 | Petersen et al. |
| 2012/0075638 A1 | 3/2012 | Rollins et al. |
| 2012/0130243 A1 | 5/2012 | Balocco et al. |
| 2012/0162660 A1 | 6/2012 | Kemp |
| 2012/0310081 A1 | 6/2012 | Adler et al. |
| 2012/0224751 A1 | 9/2012 | Kemp et al. |
| 2012/0236883 A1 | 9/2012 | Adler |
| 2012/0238869 A1 | 9/2012 | Schmitt et al. |
| 2012/0250028 A1 | 10/2012 | Schmitt et al. |
| 2012/0300215 A1 | 11/2012 | Johnson et al. |
| 2012/0300216 A1 | 11/2012 | Johnson et al. |
| 2013/0006105 A1 | 1/2013 | Furuichi |
| 2013/0010303 A1 | 1/2013 | Petersen et al. |
| 2013/0012811 A1 | 1/2013 | Schmitt et al. |
| 2013/0023761 A1 | 1/2013 | Petroff |
| 2013/0051728 A1 | 2/2013 | Petroff |
| 2013/0072805 A1 | 3/2013 | Schmitt et al. |
| 2013/0123616 A1 | 5/2013 | Merritt et al. |
| 2013/0303910 A1 | 11/2013 | Hubbard et al. |
| 2013/0310698 A1 | 11/2013 | Judell et al. |
| 2014/0018669 A1 | 1/2014 | Xu |
| 2014/0024931 A1 | 1/2014 | Winston et al. |
| 2014/0094660 A1 | 4/2014 | Tolkowsky et al. |
| 2014/0094689 A1 | 4/2014 | Cohen et al. |
| 2014/0094691 A1 | 4/2014 | Steinberg et al. |
| 2014/0094692 A1 | 4/2014 | Tolkowsky et al. |
| 2014/0094693 A1 | 4/2014 | Cohen et al. |
| 2014/0094697 A1 | 4/2014 | Petroff et al. |
| 2014/0114182 A1 | 4/2014 | Petersen et al. |
| 2014/0114184 A1 | 4/2014 | Klaiman et al. |
| 2014/0114185 A1 | 4/2014 | Tolkowsky et al. |
| 2014/0142427 A1 | 5/2014 | Petroff |
| 2014/0142432 A1 | 5/2014 | Hutchins et al. |
| 2014/0142436 A1 | 5/2014 | Hutchins et al. |
| 2014/0187929 A1 | 7/2014 | Schmitt et al. |
| 2014/0218742 A1 | 8/2014 | Adler |
| 2014/0249407 A1 | 9/2014 | Adler et al. |
| 2014/0268167 A1 | 9/2014 | Friedman et al. |
| 2014/0270445 A1 | 9/2014 | Kemp |
| 2014/0276011 A1 | 9/2014 | Schmitt et al. |
| 2014/0276020 A1 | 9/2014 | Hutchins et al. |
| 2014/0309536 A1 | 10/2014 | Douk et al. |
| 2014/0379269 A1 | 12/2014 | Schmitt |
| 2015/0153157 A1 | 6/2015 | Schmitt et al. |
| 2015/0119707 A1 | 7/2015 | Schmitt |
| 2015/0192405 A1 | 7/2015 | Schmitt |
| 2015/0238121 A1 | 8/2015 | Tu et al. |
| 2015/0297373 A1 | 10/2015 | Schmitt et al. |
| 2015/0370229 A1 | 12/2015 | Adler et al. |
| 2016/0000406 A1 | 1/2016 | Petroff |
| 2016/0022208 A1 | 1/2016 | Gopinath |
| 2016/0058307 A1 | 3/2016 | Svanerudh |
| 2016/0070066 A1 | 3/2016 | Schmitt et al. |

(56) References Cited

U.S. PATENT DOCUMENTS

| | | | |
|---|---|---|---|
| 2016/0073885 | A1 | 3/2016 | Adler |
| 2016/0174925 | A1 | 6/2016 | Dascal et al. |
| 2016/0313507 | A1 | 10/2016 | Adler et al. |
| 2016/0335763 | A1 | 11/2016 | Ambwani et al. |
| 2016/0335766 | A1 | 11/2016 | Ambwani et al. |

FOREIGN PATENT DOCUMENTS

| | | |
|---|---|---|
| WO | 2006076409 | 7/2006 |
| WO | 2007002685 | 1/2007 |
| WO | 2011038044 | 3/2011 |
| WO | 2012176191 | 12/2012 |
| WO | 2013175472 | 11/2013 |
| WO | 2014002095 | 3/2014 |
| WO | 2015136853 | 9/2015 |

OTHER PUBLICATIONS

Kassab et al., "The pattern of coronary arteriolar bifurcations and the uniform shear hypothesis," Annals of Biomedical Engineering 23 (1): 13-20, 1995.
Hariri et al., "An automatic image processing algorithm for initiating and terminating intracoronary OFDI pullback" Biomedical Optics Express 1:2 566-573 (Sep. 1, 2010).
Harrison et al., "The value of lesion cross-sectional area determined by quantitative coronary angiography in assessing the physiologic significance of proximal left anterior descending coronary arterial stenoses," Circulation 69:6 1111-1119, 1984.
Kirkeeide, "Coronary obstructions, morphology, and physiological significance," in Reiber JHC and Serruys PW (eds.), Quantitative Coronary Arteriography, Kluwer Academic Publishers, the Netherlands, 1991, pp. 229-244.
Kolyva et al., "Increased diastolic time fraction as beneficial adjunct of α1-adrenergic receptor blockade after percutaneous coronary intervention," Am J Physiol Heart Circ Physiol 295: H2054-H2060, 2008.
Kolyva et al., "'Windkesselness' of coronary arteries hampers assessment of human coronary wave speed by single-point technique," Am J Physiol Heart Circ Physiol, 295: H482-H490, 2008.
Laslett, "Normal left main coronary artery diameter can be predicted from diameters of its branch vessels," Clinical Cardiology 18 (10): 580-582, 1995.
Ofili et al., "Differential characterization of blood flow, velocity, and vascular resistance between proximal and distal normal epicardial human coronary arteries: analysis by intracoronary Doppler spectral flow velocity," Am Heart J. 130:1 37-46, 1995.
Ohta et al., "Rheological Changes After Stenting of a Cerebral Aneurysm: A Finite Element Modeling Approach," Cardiovascular and Interventional Radiology (2005) 28:768-772.
Pijls et al., "Fractional Flow Reserve (FFR) Post-Stent Registry Investigators Coronary pressure measurement after stenting predicts adverse events at follow-up: a multicenter registry", Circulation 2002; 105:2950-2954.
Seiler et al., "Basic structure-function relations of the epicardial coronary vascular tree, Basis of quantitative coronary arteriography for diffuse coronary artery disease," Circulation 85 (6): 1987-2003, 1992.
Siebes et al., "Single-wire pressure and flow velocity measurement to quantify coronary stenosis hemodynamics and effects of percutaneous interventions," Circulation 109:756-762, 2004.
Sihan et al., "A Novel Approach to Quantitative Analysis of Intravascular Optical Coherence Tomography Imaging," Computers in Cardiology 2008; 35:1089-1092.
Sihan et al., "Fully Automatic Three-Dimensional Quantitative Analysis of Intracoronary Optical Coherence Tomography: Method and Validation," Catheterization and Cardiovascular Interventions 74:1058-1065 (2009).
Spaan, "Coronary Blood Flow," Ch 12. Dordrecht, The Netherlands: Kluwer Acedemic Publishers, Boston; 1991: pp. 333-361.
Takagi et al., "Clinical potential of intravascular ultrasound for physiological assessment of coronary stenosis," Circulation 100: 250-255, 1999.
Verhoeff et al., "Influence of percutaneous coronary intervention on coronary microvascular resistance index," Circulation 111:76-82, 2005.
White et al., "Does visual interpretation of the coronary angiogram predict the physiologic importance of coronary stenoses?," N. Engl J Med 310:13 819-824, 1984.
Wilson et al., "Prediction of the physiologic significance of coronary arterial lesions by quantitative lesion geometry in patients with limited coronary artery disease," Circulation 75: 723-732, 1987.
Perez-Rovira et al., "Deformable Registration of Retinal Fluorescein Angiogram Sequences Using Vasculature Structures", 32nd Annual Conf. of IEEE EMBS, 2010, pp. 4383-4386.
Herrington et al., "Semi-automated boundary detection for intravascular ultrasound," Computers in Cardiology 1992 Proceedings., pp. 103-106, Oct. 1992.
Sonka et al., "Segmentation of intravascular ultrasound images: a knowledge-based approach," IEEE Transactions on Medical Imaging, 14(4):719-732, Dec. 1995.
Mojsilovic et al., "Automatic segmentation of intravascular ultrasound images: A texture-based approach," Annals of Biomedical Engineering, 25:1059-1071, Nov. 1997.
Gil et al., "Automatic segmentation of artery wall in coronary IVUS images: a probabilistic approach," Computers in Cardiology 2000; 27:687-690.
Haas et al., "Segmentation of 3D intravascular ultrasonic images based on a random field model," Ultrasound in Medicine & Biology, 26:2, 297-306, 2000.
Kovalski et al., "Three-dimensional automatic quantitative analysis of intravascular ultrasound images," Ultrasound in Medicine & Biology, 26(4):527-537, 2000.
Pujol et al., "Intravascular Ultrasound Images Vessel Characterization using AdaBoost," Functional Imaging and Modeling of the Heart: Lecture Notes in Computer Science, pp. 242-251, 2003.
Taki et al., "Automatic segmentation of calcified plaques and vessel borders in IVUS images," International Journal of Computer Assisted Radiology and Surgery, 3(3-4):347-354, Sep. 2008.
van den Berg et al., "Using three-dimensional rotational angiography for sizing of covered stents," Am. J. Roentgenology, 178:149-152 (2002).
Wong et al., "A novel method of coronary stent sizing using intravascular ultrasound: safety and clinical outcomes," Int. J. Angiol., 18(1): 22-24 2009.
Bonnema et al., "An automatic algorithm for detecting stent endothelialization from volumetric optical coherence tomography datasets", Physics in Medicine and Biology, 53 :12, Jun. 21, 2008, pp. 3083-3098.
Unal et al., "Stent implant follow-up in intravascular optical coherence tomography images," Int J Cardiovasc Imaging, DOI 10.1007/s10554-009-9508-4, published online Sep. 24, 2009, 8 pgs.
Xu et al., "Characterization of atherosclerosis plaques by measuring both backscattering and attenuation coefficients in optical coherence tomography," Journal of Biomedical Optics, 13:3, May/Jun. 2008, 8 pgs.
Takano et al.. "Evaluation by Optical Coherence Tomography of Neointimal Coverage of Sirolimus-Eiuting Stent Three Months After Implantation," American Journal of Cardiology, vol. 99, No. 8, Apr. 14, 2007, pp. 1033-1038.
Tung et al., "Automatic Detection of Coronary Stent Struts in Intravascular OCT Imaging," Proceedings of SPIE, vol. 8315, Feb. 22, 2012 (8 pgs.).
Shengxian Tu et al., "In vivo comparison of arterial lumen dimensions assessed by co-registered three-dimensional (3D) quantitative coronary angiography, intravascular ultrasound and optical coherence tomography", Int. J. Cardiovasc Imaging (2012) 28:1315-1327.
Palti-Wasserman et al., "Identifying and Tracking a Guide Wire in the Coronary Arteries During Angioplasty from X-Ray Images", IEEE transactions on biomedical engineering, 44:2, Feb. 1997, pp. 152-164.

(56) References Cited

OTHER PUBLICATIONS

Dave Fornell, "The Advantages and Disadvantages of OCT vs. IVUS", Diagnostic and Interventional Cardiology, May 18, 2011, pp. 1-4.
Lansky et al., "Quantitative Angiographic Methods for Bifurcation Lesions: A Consensus Statement from the European Bifurcation Group", Catherization and Cardiovascular Interventions 73:2 (Feb. 1, 2009) pp. 258-266.
Zhang et al., "Coronary Bifurcation Intervention: What Role Do Bifurcation Angles Play?", Journal of Interventional Cardiology, 28:3 (Jun. 9, 2015) pp. 236-248.
PCT International Search Report for International Application No. PCT/2016/056216 dated Jan. 23, 2017 from the International Searching Authority (5 pages).
PCT Written Opinion of the International Searching Authority for International Application No. PCT/2016/056216 dated Jan. 23, 2017 from the International Searching Authority (11 pages).

\* cited by examiner

INTRAVASCULAR IMAGING USER INTERFACE SYSTEMS AND METHODS

CROSS-REFERENCE TO RELATED APPLICATIONS

This application claims priority to U.S. Provisional Patent Application No. 62/241,056 filed on Oct. 13, 2015, the disclosure of which is herein incorporated by reference in their entirety.

BACKGROUND

Coronary artery disease is one of the leading causes of death worldwide. The ability to better diagnose, monitor, and treat coronary artery diseases can be of life saving importance. Intravascular optical coherence tomography (OCT) is a catheter-based imaging modality that uses light to peer into coronary artery walls and generate images thereof for study. Utilizing coherent light, interferometry, and micro-optics, OCT can provide video-rate in-vivo tomography within a diseased vessel with micrometer level resolution. Viewing subsurface structures with high resolution using fiber-optic probes makes OCT especially useful for minimally invasive imaging of internal tissues and organs. This level of detail made possible with OCT allows a clinician to diagnose as well as monitor the progression of coronary artery disease. OCT images provide high-resolution visualization of coronary artery morphology and can be used alone or in combination with other information such as angiography data and other sources of subject data to aid in diagnosis and planning such as stent delivery planning OCT imaging of portions of a patient's body provides a useful diagnostic tool for doctors and others. For example, imaging of coronary arteries by intravascular OCT may reveal the location of a narrowing or stenosis. This information helps cardiologists to choose between an invasive coronary bypass surgery and a less invasive catheter-based procedure such as angioplasty or stent delivery. Although a popular option, stent delivery has its own associated risks.

A stent is a tube-like structure that often is formed from a mesh. It can be inserted into a vessel and expanded to counteract a stenotic condition that constricts blood flow. Stents typically are made of a metal or a polymer scaffold. They can be deployed to the site of a stenosis via a catheter. During a cardiovascular procedure, a stent can be delivered to the stenotic site through a catheter via a guide wire, and expanded using a balloon. Typically, the stent is expanded using a preset pressure to enlarge the lumen of a stenosed vessel. Angiography systems, intravascular ultrasound systems, OCT systems, in combinations or alone can be used to facilitate stent delivery planning and stent deployment.

There are several factors that influence the patient outcome when deploying stents. In some procedures, the stent should be expanded to a diameter that corresponds to the diameter of adjacent healthy vessel segments. Stent overexpansion may cause extensive damage to the vessel, making it prone to dissection, disarticulation, and intra-mural hemorrhage. Stent under expansion may inadequately expand the vessel. If the portions of the stent fail to contact the vessel wall, the risk of thrombosis may increase. An under-inflated or malapposed stent may fail to restore normal flow. Once a stent is installed, stent malapposition and under expansion of the stent can result in various problems. In addition, flow-limiting stenoses are often present in the vicinity of vascular side branches. Side branches can be partially or completely occluded or "jailed" by stent struts when a stent is deployed in a main vessel to address a stenosis or other malady. Side branches are vital for carrying blood to downstream tissues. Thus, jailing can have an undesired ischemic impact. The ischemic effects of jailing are compounded when multiple side branches are impacted or when the occluded surface area of a single branch is significant.

The present disclosure addresses these challenges and others.

SUMMARY

In part, the disclosure relates to computer-based methods and systems to transform intravascular data to facility diagnostic review and research. In one embodiment, the disclosure relates to systems and methods to generate visualizations of a carina in coronary bifurcations. The method and various steps of the method can be performed automatically which can include in response to one or more user actions.

In part, the disclosure relates to the display of various views of an artery generated in response to intravascular data collected during a pullback using a probe. The display of one or more cross-sectional or three-dimensional or cut plane views, in response to a user selection, facilitates evaluation of one or more carinas in a blood vessel and can automatically be toggled between using a user interface control in one embodiment. The ability to toggle a carina view on and off is also an advantages diagnostic feature. Further, the ability to jump or otherwise move between different carinas along a vessel save time and facilitates comparison of different intravascular features.

In part, the disclosure relates to a method of detecting a region of a side branch of a blood vessel. The method includes identifying a subset of image frames that include a side branch of a blood vessel from a set of image frames of intravascular data; calculating a midpoint angle of side branch opening in each frame of the subset of image frames; calculating a median angle of the side branch opening using the midpoint angles calculated for each frame of the subset of image frames; and determining a visualization plane for viewing the side branch using the calculated median angle to allow for detection of a region associated with the side branch. In one embodiment, the detected region associated with the side branch includes a carina. In one embodiment, the method further includes displaying the region oriented relative to the viewing plane.

In one embodiment, the region comprises a carina. In one embodiment, the method further includes generating a control signal to active a carina view in response to a user action. In one embodiment, the method further includes generating a control signal to active a carina view in response to a user action. In one embodiment, the method further includes automatically orienting a user view of the region in a cross-sectional viewing mode of a user interface. In one embodiment, the method further includes automatically orienting a user view of the region in a three dimensional viewing mode of a user interface. In one embodiment, the method further includes automatically orienting a user view of the region in response to activation of a user interface toggle.

In part, the disclosure relates to a computer-based system for detecting a region associated with a side branch of a vessel. The system includes a processor including one or more image detection software modules that is configured to process a plurality of images frames obtained from an optical coherence tomography pullback with respect to a blood vessel using a data collection probe, the image detection software modules being configured to process the image frames to detect one or more side branches of the blood vessel and calculate an angle of an opening of the side branch for each image frame in which a side branch is detected; one or more memory devices configured to store the calculated angles to be used by the image detection software modules to calculate a median angle for the opening of each side branch detected in the image frames; and a display in communication with the processor for displaying one or more views of the data in the image frames; wherein the median angle for each side branch is configured to determine a visualization plane for each side branch to allow the display to show an optical view of each side branch for detection of a region of the side branch. In one embodiment, the detected region of the side branch includes a carina. In one embodiment, the detected region of the side branch includes a stent portion and a side branch portion.

In part, the disclosure relates to a method of detecting a region of a side branch of a blood vessel. The method includes accessing a set of intravascular data stored in machine readable memory; performing side branch detection with regard to the intravascular data to identify one or more side branches; identifying a plurality of frames for the one or more side branches; determining a consistent reference angle value for each of the plurality of frames; statistically analyzing the plurality of consistent references angles using a statistical measure applied to the plurality of consistent reference angles; and selecting an overall statistically analyzed angle as a cut plane viewing angle for a representation of the blood vessel generated on a display having a user interface.

In one embodiment, the method further includes generating one or more visual presentations of a blood vessel segment using the intravascular data. In one embodiment, the method further includes automatically generating visualizations of one or more carinas in coronary bifurcations that are viewable using the overall statistically analyzed angle. In one embodiment, the statistical measure is selected from the group consisting of a mean, a median, a mode, and a weighted average and a histogram. In one embodiment, the overall statistically analyzed angle is a median angle for a plurality of midpoint angles. In one embodiment, the method further includes controlling an "on" and "off" state of automatic display using the overall statistically analyzed angle via a user interface feature on a display of the representation of the intravascular data.

BRIEF DESCRIPTION OF DRAWINGS

The figures are not necessarily to scale, emphasis instead generally being placed upon illustrative principles. The figures are to be considered illustrative in all aspects and are not intended to limit the disclosure, the scope of which is defined only by the claims.

DETAILED DESCRIPTION

Figure 1:
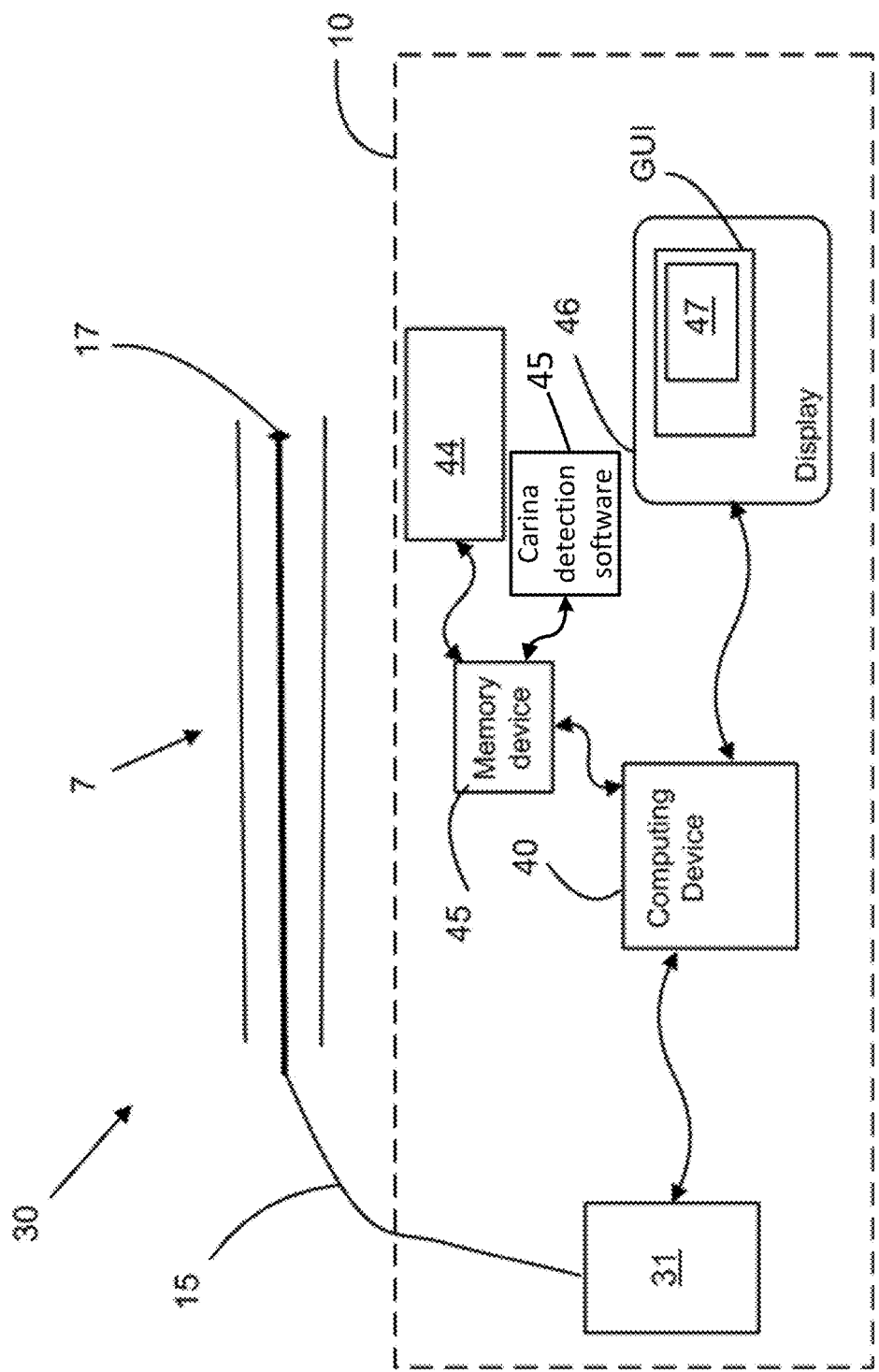
FIG. 1 shows a schematic diagram of an intravascular imaging and data collection system in accordance with an illustrative embodiment of the disclosure.

In one aspect, a method is provided to visualize one or more intravascular regions of interest in a computer-generated representation of a blood vessel. In various embodiments, the method includes determining one or more viewing perspectives of one or more side branches of a blood vessel representation. The blood vessel representation can be generated using intravascular image data such as obtained by an optical or acoustic data collection probe.

In part, the disclosure relates to diagnostic and display methods relating to one or more features associated with a side branch. In particular, the disclosure, in one embodiment, relates to displaying and adjusting one or more views relative to branching artery such as a coronary bifurcation, or one or more subsections or regions thereof. The subsections or regions thereof can include the flow divider that is the tissue wall or membrane that separates the two vessel segments that constitute the bifurcation. This flow divider or the tissue region associated with the origin of the bifurcation is referred to herein as a carina.

Visualizing the side branches of the vessel and detecting one or more regions or frames in the vicinity of the side branch, for example can be used to locate one or more carinas associated with a side branch or bifurcation. In turn, the process of visualizing a carina can be used to identify locations along the blood vessel at which the potential for stenting over or jailing a side branches poses a greater risk to a patient in light of the presence of a carina.

With this diagnostic tool, deploying a stent in a blood vessel can be achieved by having a roadmap that indicates the location of side branches and carinas and also provides various enhanced viewing modes to facilitate the diagnostic assessment of such blood vessel features. During stent placement, it is important to determine a viewing angle for locating a carina, which can be achieved based on the angle at which the side branch joins a main vessel. As described in more detail herein, a user can use the diagnostic tools and vessel representations generated from intravascular measurements and select or toggle a display view of one or more carinas near a side branch of the blood vessel. This is of significant importance when the side branch is a major source of perfusing blood flow such that blocking it with a stent is a problematic scenario and blocking it was a portion of a carina and a stent represents and even worse potential scenario.

In part, the disclosure relates to intravascular data collection systems, such as OCT, IVUS, and angiography systems and the exchange of data between two or more of the foregoing, as examples, and the generation and display of diagnostic information such as indicators. In one embodiment, intravascular data such as OCT is collected while angiography data is simultaneously collected. Indicators can include one or more one or two dimensional graphic elements and one or more associated indicia such as color, gray scale or other scale gradations, hashes, symbols or other visual elements.

One or more indicators can be generated and displayed such as by overlaying or otherwise combining such indicators with images generated using an intravascular data collection system. The indicators can include longitudinal, cross-sectional, and other indictor types such as one or more indicia or graphical elements suitable for indicating diagnostic information of interest such as tracking relative to user selected landmarks. Stent strut indicators can also be used. In addition, shadows and other elements which can be misconstrued as dissections, side branches or other vessel features can be shaded or otherwise changed to distinguish them and facilitate user review and analysis of images frames and data.

Suitable diagnostic information can include stent apposition information such as the malapposition of a stent relative to a vessel wall or lumen boundary, user selected OCT positions in a vessel and associated angiography frame locations, and other intravascular diagnostic information or other information generated to facilitate stent delivery planning. The system includes a processor in communication with the graphical user interface and configured to send commands to the graphical user interface. One or more software programs are used to perform one or more of the following: co-register data such as frames of image data, generate and display longitudinal indicators indicative of stent position relative to a determined lumen boundary, translate user selected OCT position information to an angiography display using one or more graphical elements to facilitate co-registration, and visually identifying stents and simulated stents for planning purposes and others as described herein. Various three-dimensional fly through views can also be toggled on and off to facilitate diagnostic review and stent planning as described herein.

In part, the disclosure relates to a graphical user interface (GUI) element or indicator that is represented on a display relative to subject data such as image data or other intravascular parameters measured relative to the subject. Any clinically useful parameter as it changes longitudinally or cross-sectionally during the course of an Optical Coherence Tomography pullback recording or IVUS or other intravascular or angiography system can be evaluated and displayed as an indicator. The element can be used by interventional cardiologists to quickly see clinically useful information for an entire pullback recording in a single view without needing to manually manipulate the image. The indicator can guide a user to the particular points of interest in the vessel based on the parameter exceeding or falling below a clinically meaningful threshold value. By encoding the parameter value in a continuous color map, or other scale using suitable indicia for example, varying degrees of severity of the parameter can be easily summarized for the entire vessel in one easy to interpret view. These features are shown with the various apposition bars, stent indicators, and other indicators for angiography images and other intravascular data collection images.

Also disclosed herein are systems and methods for visualizing stents and other medical devices in bifurcated vessels. Using a combination of detected side branch locations, lumen contours, and stent strut positions, a viewing angle that looks along the direction of the side branch opening and into the main vessel can be provided. This provides a clear user display for a clinician to evaluate a treatment site for optimal stent placement, and to assess whether further intervention, such as stent modification, is required.

It may be necessary to open a group of cells in a deployed stent using a balloon in order to improve blood flow in the jailed side branch. The balloon guidewire typically is introduced into the jailed side branch ostium in as distal (e.g., downstream) a position as possible. Obtaining a distal guidewire position will lead to the stent struts being pushed to the proximal (e.g., upstream) side of the side branch ostium, which minimizes flow disruptions at the higher-flow distal side of the ostium. Clear, rapid visualization of guidewire position in relation to the stent and side branch is therefore clinically advantageous.

As shown in FIG. 1, a data collection system 30 for use in collecting intravascular data includes a data collection probe 7 that can be used to image a blood vessel. A guidewire can be used to introduce the probe 7 into the blood vessel. The data collection probe 7 can be introduced and pulled back along a length of a blood vessel 5 while collecting data. As the optical fiber is retracted (pulled-back) along the length of the vessel, a plurality of scans or OCT data sets are collected as the probe or a portion thereof rotates. This is referred to as a pullback in one embodiment. These data sets, or collections of frames of image data, can be used to identify regions of interest such as a stenosis or a deployed stent. In one embodiment, the data collection probe 7 is an OCT probe configured for use with an OCT system 10 that includes an interferometer and a data processing system. The distance measurements collected using the OCT probe 7 can be processed to generate frames of image data such as cross-sectional views or longitudinal views (L-mode views) of the blood vessel. For clarity, a cross-sectional view can include without limitation a longitudinal view. These images can be processed using one or more image data processing modules or stages.

The probe 7 is shown prior to or after insertion in a blood vessel. The probe 7 is in optical communication with an OCT system 10. The OCT system or subsystem 10 that connects to probe 17 via an optical fiber 15 can include a light source such as a laser, an interferometer having a sample arm and a reference arm, various optical paths, a clock generator, photodiodes, and other OCT system components.

In one embodiment, an optical receiver 31, such as a balanced photodiode based system, can receive light exiting the probe 7. A computing device 40 such as a computer, processor. ASIC, or other device can be part of the OCT system 10 or can be included as a separate subsystem in electrical or optical communication with the OCT system 10. The computing device 40 can include memory, storage, buses and other components suitable for processing data and software 44 such as image data processing stages configured for stent visualization, stent malapposition detection, carina display, and pullback data collection.

In one embodiment, the computing device 40 includes or accesses software modules or programs 44, such as a side branch detection module, a guide wire detection module, a lumen detection module, a stent detection module, a median mask clearing module, an intensity averaging module, a stent malapposition detection module, and other software modules. For example, the computing device 40 can access a carina detection module 45 for detecting the existence of a carina at the location of each side branch along the vessel. The carina or bifurcation detection software 45 can also include or be in communication with user interface software components to toggle carina views on and off and to display and toggle the various user interface display modes such as stent planning, fly through and other viewing modes described herein. The software modules or programs 44 can include an image data processing pipeline or component modules thereof and one or more graphical user interfaces (GUI). An exemplary image processing pipeline is used for transforming collected OCT data into two dimensional and three dimensional views of blood vessels and stents. The image data processing pipeline or any of the methods described herein are stored in memory and executed using one or more computing devices such as a processor, device, or other integrated circuit.

As shown in FIG. 1, a display 46 can also be part of the system 10 for showing information 47 such as cross-sectional and longitudinal views of a blood vessel generated using collected OCT data. System 10 can be used to display image data relating to one or more carinas associated with detected side branches for the vessel. In one embodiment, one or more steps can be performed automatically or without user input other than initial user input to navigate relative to one or more images, enter information, select or interact with an input such as a controller or user interface component, or otherwise indicate one or more system outputs. In one embodiment, a carina view is presented as an option to select to facilitate review of a two or three-dimensional view of a representation of the vessel and one or more carinas associated with a sidebranch. Toggling between one or more viewing modes in response to user inputs can be performed relative to various steps described herein.

The OCT-based information 47 can be displayed using one or more graphic user interface(s) (GUI). In addition, this information 47 can include, without limitation, cross-sectional scan data, longitudinal scans, diameter graphs, image masks, shadow regions, stents, areas of malapposition, lumen border, perpendicular distances measured relative to a automatically detected lumen border and a perpendicular distance extending from the lumen border to a detected stent strut position, and other images or representations of a blood vessel or the underlying distance measurements obtained using an OCT system and data collection probe.

The computing device 40 can also include software or programs 44, which can be stored in one or more memory devices 45, configured to identify stent struts and malapposition levels (such as based on a threshold and measured distance comparison) and other blood vessel features such as with text, arrows, color coding, highlighting, contour lines, or other suitable human or machine readable indicia.

The display 46 depicts various views of the blood vessel, in accordance with an embodiment. The display can include a menu for showing or hiding various features, such as a menu for selecting blood vessel features to display, and a menu for selecting the virtual camera angle of the display. The user can toggle between multiple view angles on the user display. In addition, the user can toggle between different side branches on the user display, such as by selecting particular side branches and/or by selecting a view associated with a particular side branch. For example, the user can select an ostium view, which can be the default view in one embodiment, or a carinal/carina view to allow them to view a carina for one or more side branches. In one embodiment, the image processing pipeline and associated software modules detect the lumen boundary and the side branches in the artery imaged using the data collected during a pullback. In one embodiment, the carina view can be selected or be the default view when a carina is displayed. It can be toggled on or off in various embodiments. By selecting the carinal view, the views of the vessel on the display will snap to that calculated cut plane, as discussed in more detail below.

Figure 4:
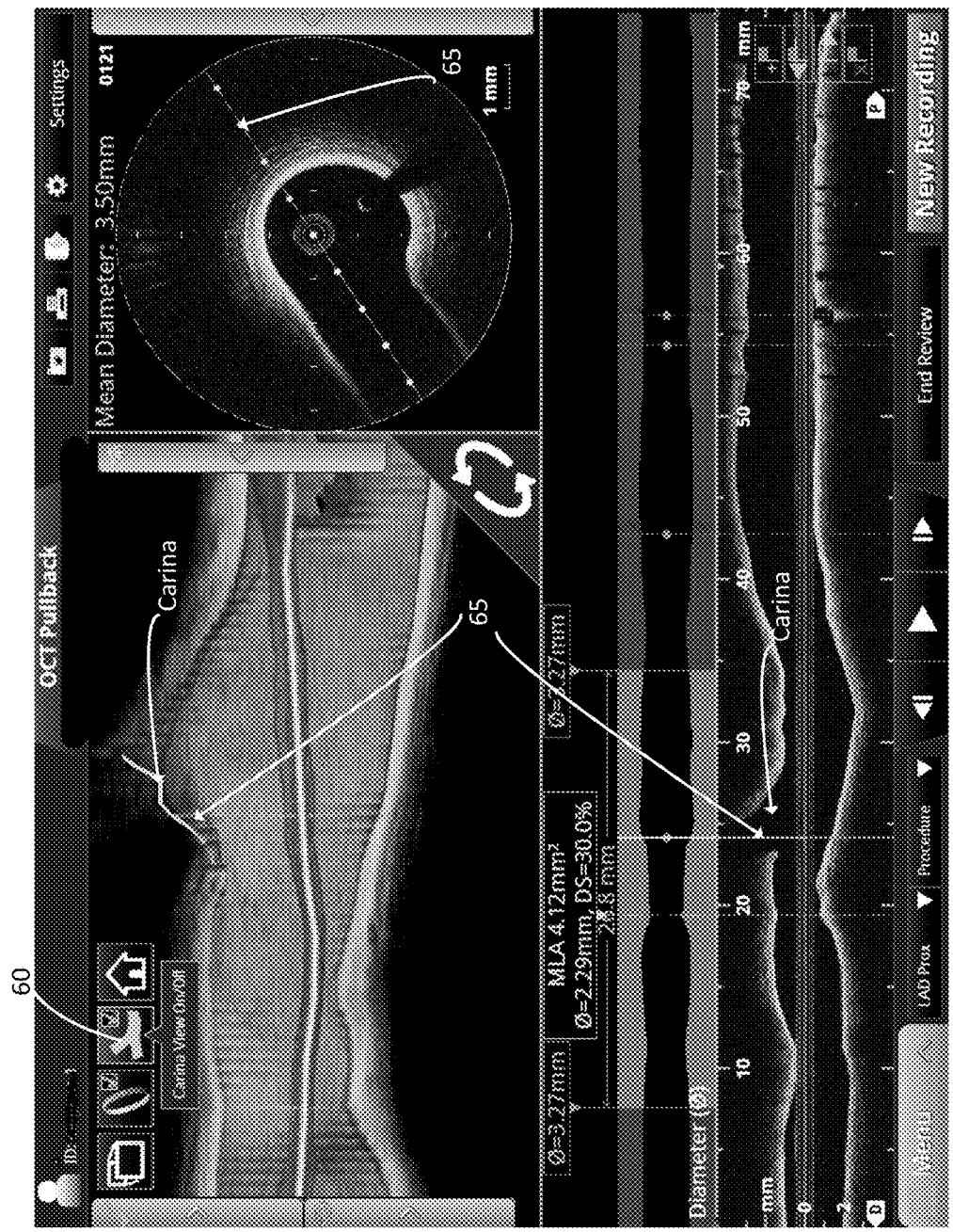
FIGS. 4 and 5A show various user interfaces and data representations including various viewing and image orienting features relative to one or more imaging modalities in accordance with an illustrative embodiment of the disclosure.
Figure 5A:
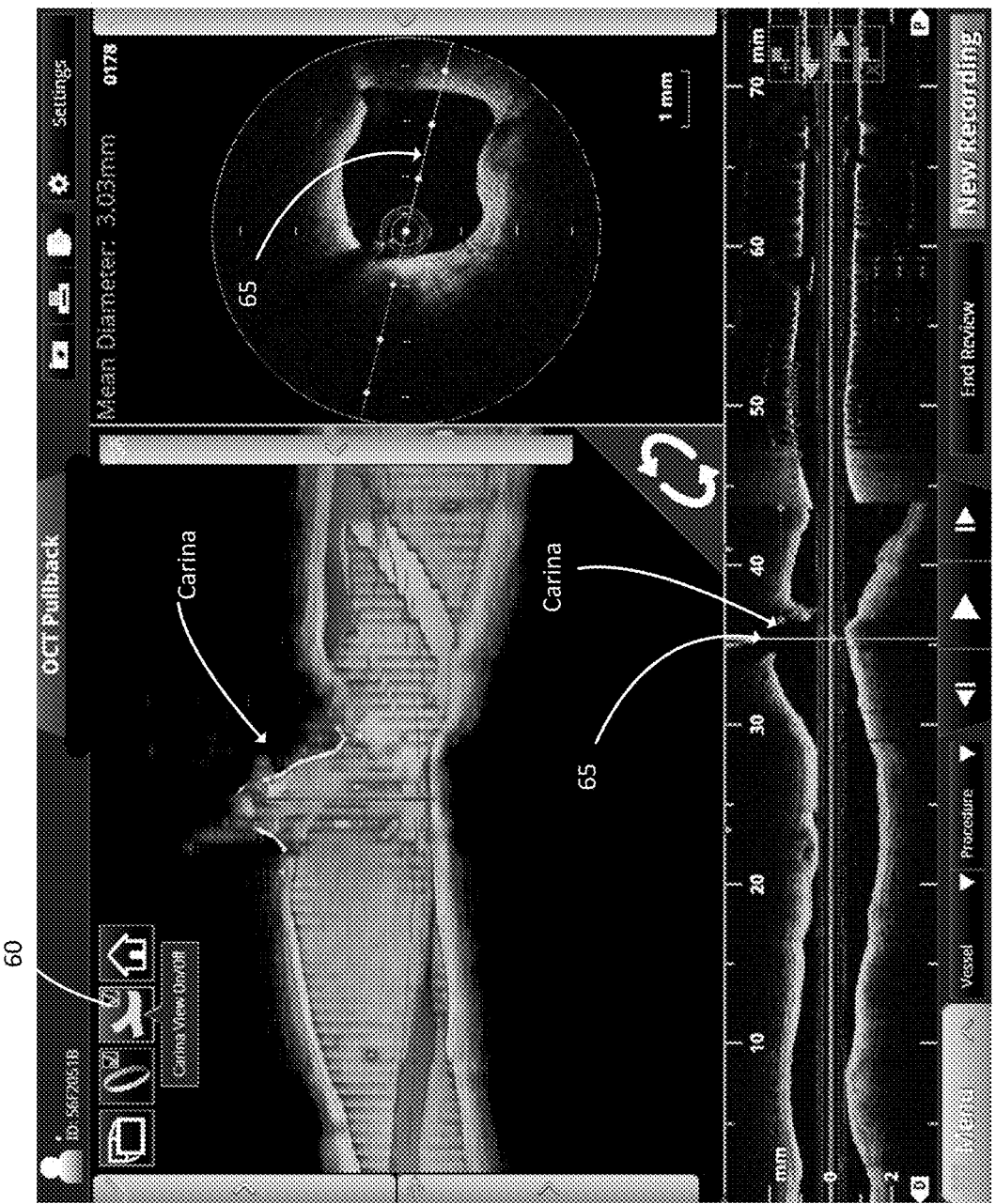
Figure 5B:
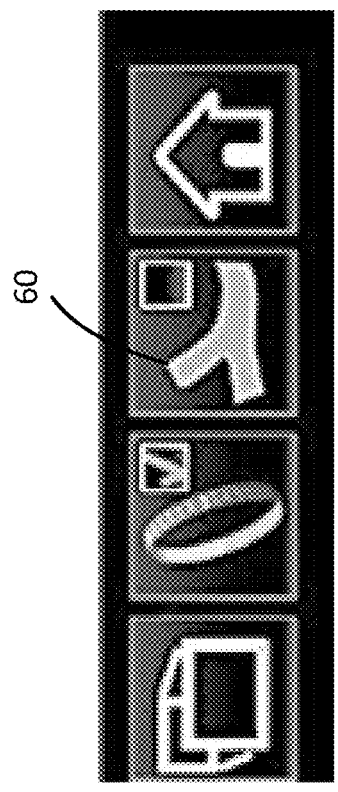
FIGS. 5B and 5C show user interfaces components suitable for toggling between carina views and other data representations including various viewing and image orienting features relative to one or more imaging modalities in accordance with an illustrative embodiment of the disclosure.
Figure 5C:
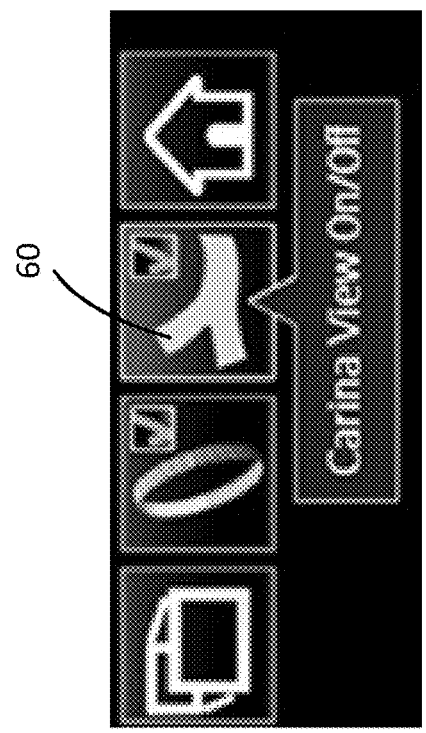

Once the OCT data is obtained with a probe and stored in memory; it can be processed to generate information 47 such as a cross-sectional, a longitudinal, and/or a three-dimensional view of the blood vessel along the length of the pullback region or a subset thereof. These views can be depicted as part of a user interface as shown in FIGS. 4-5B. The images of the blood vessel generated using the distances measurements obtained from the OCT system provide information about the blood vessel and objects disposed therein.

Accordingly, in part, the disclosure relates to software-based methods and related systems and devices suitable for evaluating and depicting information regarding a blood vessel, a stent or other vascular information of interest. The OCT data can be used to generate 2-D views such as cross-sectional and longitudinal views of a blood vessel before or after an initial stent deployment or corrective stent related procedure. The OCT data obtained using a data collection probe and various data processing software modules can be used to identify, characterize, and visualize a stent and/or one or more properties relating to the stent and/or the lumen in which it is disposed.

Stent position relative to the wall of the blood vessel and in relation to openings for side branches in the wall of the blood vessel can be visualized such that the side branch openings are not blocked by the stent. In one embodiment, side branches that include a carina are identified and visualized to aide in stent placement to prevent the stent from pushing the carina and blocking the opening to the side branch. In one embodiment, identifying and/or visualizing a carina is accomplished by determining a visual cut plane for viewing the side branch to allow an optimized view of a carina such that a used can visualize the carina in a cross-sectional or three-dimensional view of a blood vessel.

Figure 2A:
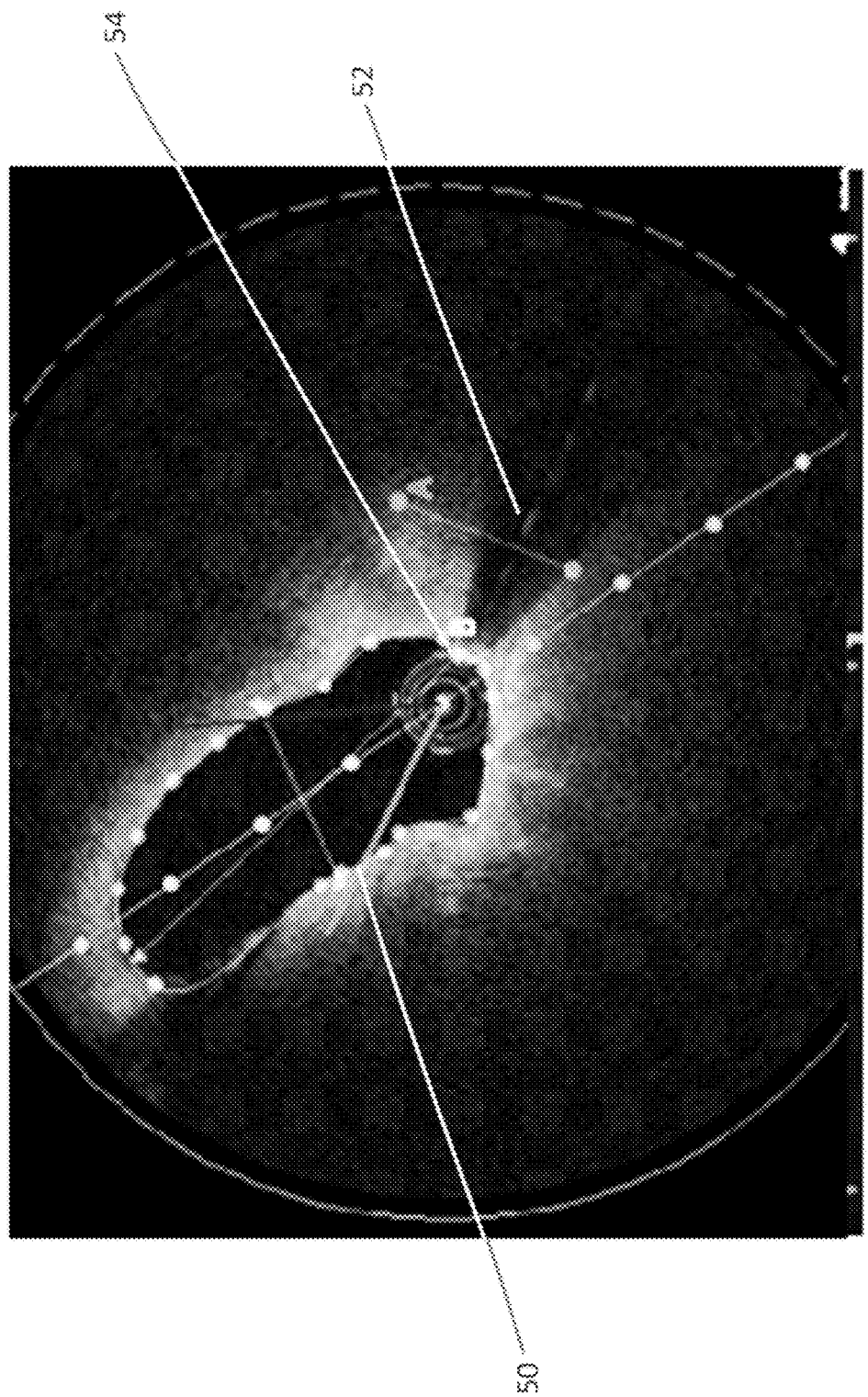
FIGS. 2A-3 show additional details relating to user interface displays and intravascular data collection systems and indicators suitable therewith and angiography systems for diagnostic processes including stent delivery planning in accordance with an illustrative embodiment of the disclosure.
Figure 2B:
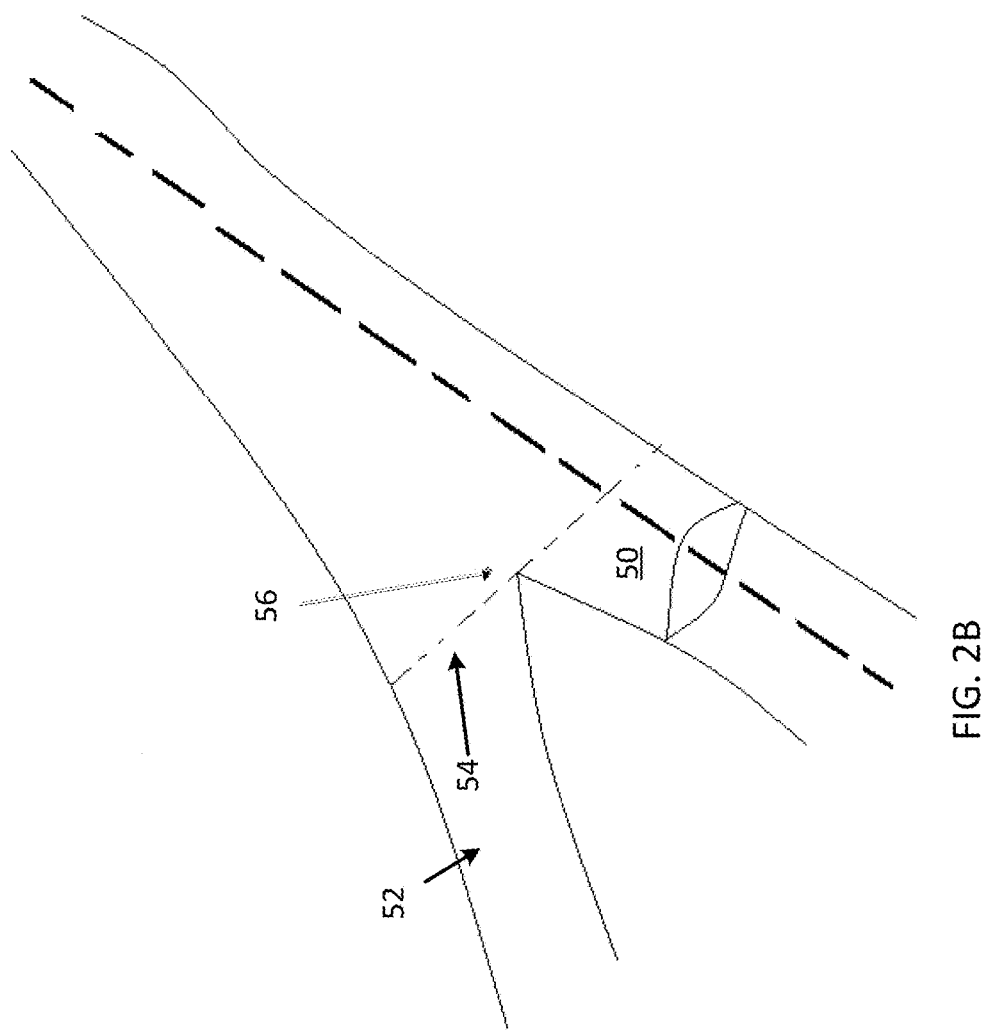
Figure 3:
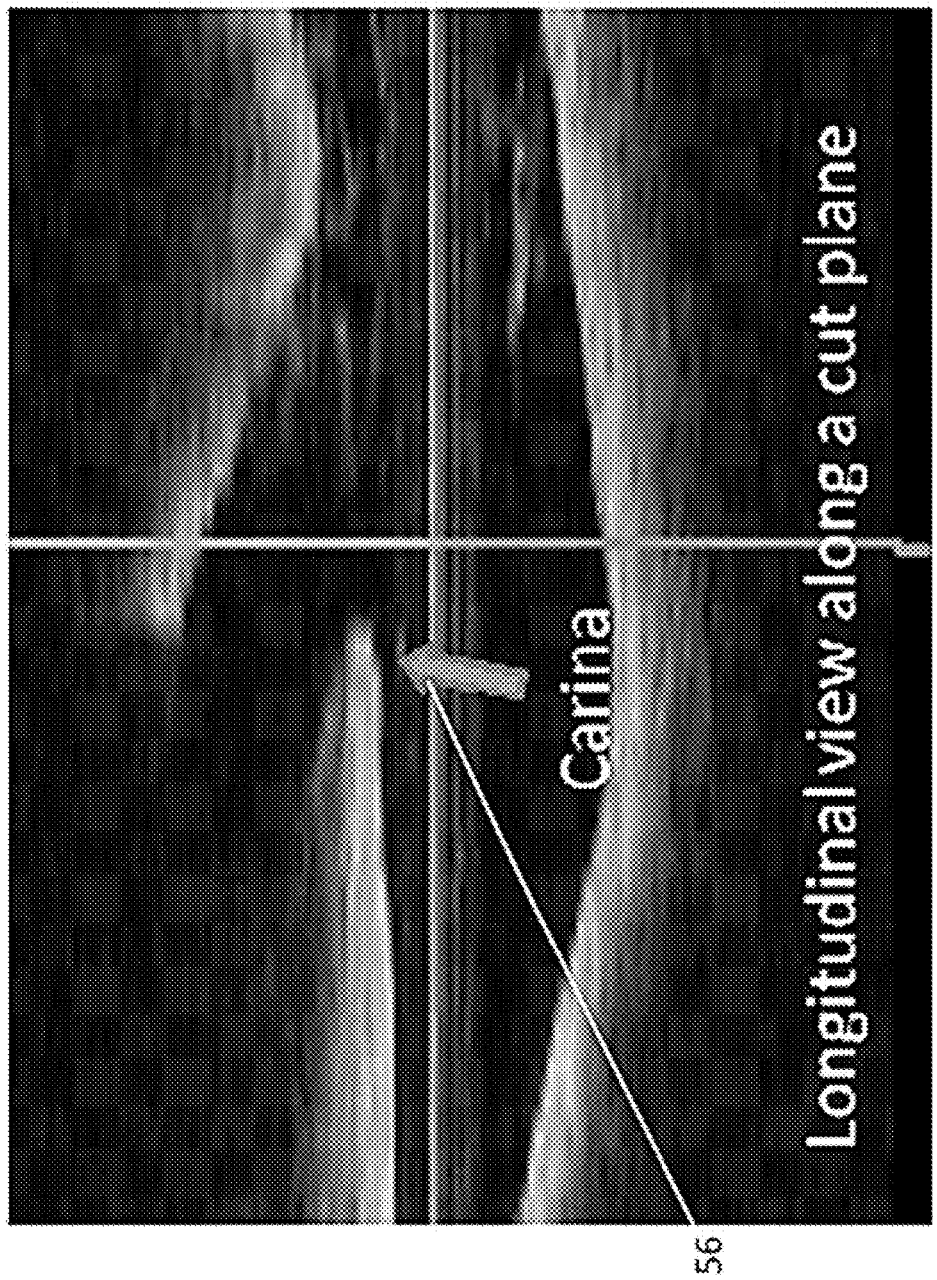

FIGS. 2A-C show views of a vessel 50 and an opening 54 of a side branch 52 that includes a carina 56. FIG. 2B is a schematic diagram of the vessel 50 and shows the junction or bifurcation of vessel 50 and side branch 52. In FIG. 2A, the opening 54 to the side branch 52 is visible at a location labeled B in a cross sectional view, which is also shown in longitudinal view in FIG. 3. The carina 56 is visible as a lip or flap at the location of the opening 54 of the side branch 52 in FIG. 3. In FIG. 2B, the carina 56 is shown as the flap or lip in between vessel 50 and branch 52. The placement of a stent at a location of a carina 56 must be done to avoid the carina 56 blocking off the opening 54 of the side branch 52.

FIGS. 4-5B illustrate exemplary user interfaces as can be displayed to a user on the display 46 shown in FIG. 1. FIGS. 4-5B show an interface with a longitudinal view or L-mode that depicts a longitudinal view of the vessel through which the probe is pulled through. The display also includes a cross sectional view of the vessel as a selected cut plane. The display includes controls that allow the user to control the images on the display. In one embodiment, the display includes a toggle button 60 for controlling a carina view. This switches the images on the display to show the carina of a side branch using a cut plane such that the user is given an optimized view of the carina. In addition to toggling to the carina view, the user can toggle through all the detected side branches and view either the ostium view or the carinal view for carina detection.

In order to generate a visualization of a region of a side branch, for example, that includes a carina, branch detection algorithms are used to determine subsets of the data sets, or frames of image data, that include a side branch. Thus, for all of the frames collected by the probe 7 during pullback through a vessel, subsets of frames are identified that are determined to include a side branch off the main vessel. For each frame in the subset, a midpoint angle of the side branch opening is calculated and used to determine a median angle of the branch opening, discussed in more detail below. The calculated median angle is used to determine a cut plane for optimized visualization of the region around the opening for each side branch found in the subset of frames. The carina view is toggled on in FIGS. 4 and 5A. In FIG. 4, the vertical reference 65 is positioned at the carina in the top left and top right panels and in the two horizontal user interface panels below. The reference and carina views are also shown in FIG. 5A with vertical reference 65.

The top left panel shows a cut through three dimensional view with the carina in the top region of the panel. The automatic detection of carinas and selective viewing angles as well as the ability to navigate between them simplifies and speeds review by an end user. This can result in improved feedback and diagnostic information for a patient. FIG. 5B shows s carina view user interface 60 from FIGS. 4 and 5A. The interface 60 is actionable via a user interaction to toggle one or more carina views on and off. The user interface control 60 can be used to turn the view on as shown by the check mark or off as shown by the empty unchecked square. This gives the end user an easy way to control and streamline their diagnostic review. A user can toggle the carina view 60 on and off with a mouse click, joystick button, remote pointer, touch screen control or other user based input devices.

The use of arrow heads showing directionality in a given figure or the lack thereof are not intended to limit or require a direction in which information can flow. For a given connector, such as the arrows and lines shown connecting the elements shown in FIG. 1, for example, information can flow in one or more directions or in only one direction as suitable for a given embodiment. The connections can include various suitable data transmitting connections such as optical, wire, power, wireless, or electrical connections.

One or more software modules can be used to process frames of information received from the system shown in FIG. 1. Various software modules which can include without limitation software, a component thereof, or one or more steps of a software-based or processor executed method can be used in a given embodiment of the disclosure. The user interface 60 operates to navigate through various panels of intravascular data generated and processed using the system of FIG. 1.

Figure 6:
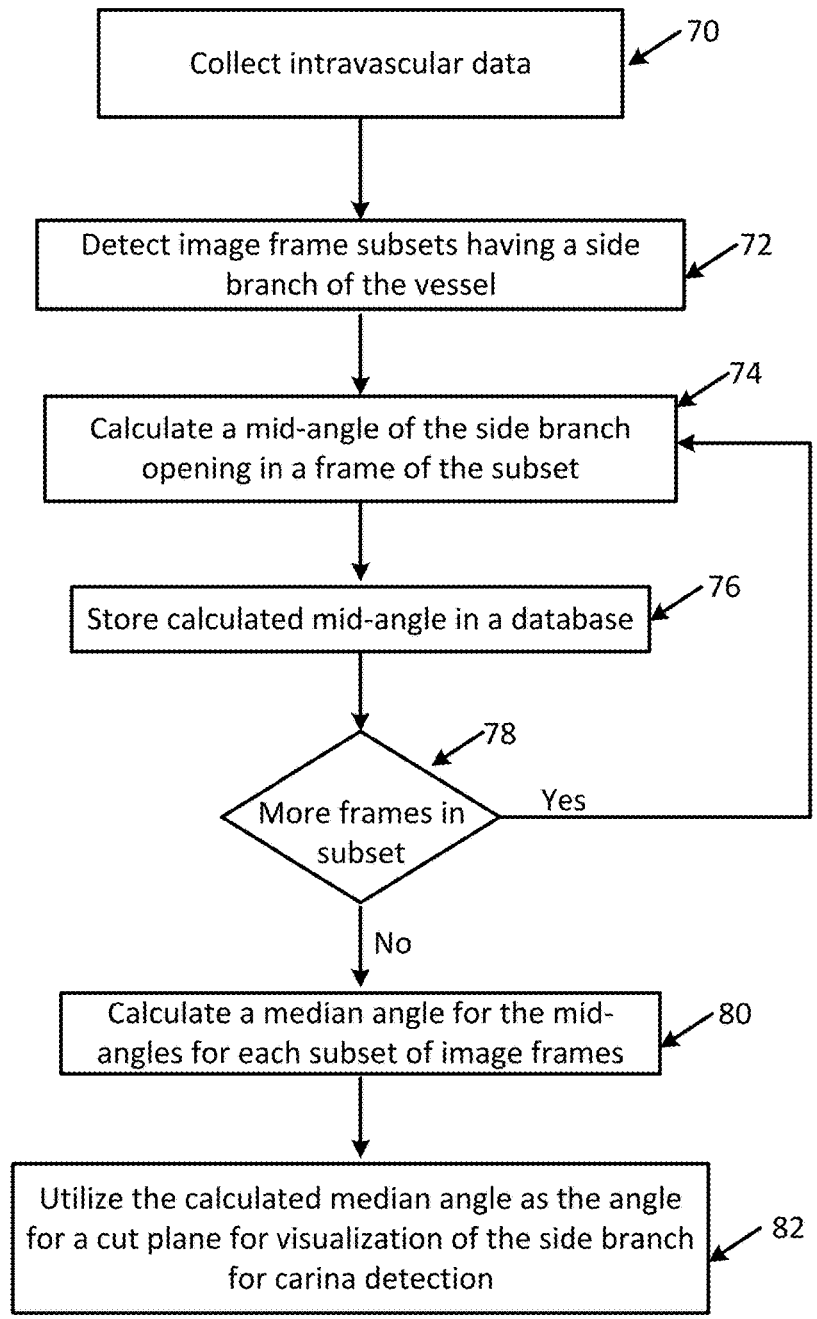
FIG. 6 is a flowchart illustrating a method of carina visualization and detection for each side branch of a main vessel with an illustrative embodiment of the disclosure.

FIG. 6 illustrates a flowchart of a method for providing visualization of a region of a side branch of a main vessel, for example, to visual features of the region that can include a carina. In step 70, intravascular data is collected using a probe, such as the probe 7 of FIG. 1, in the form of image frames of a vessel. In one embodiment, in step 70, intravascular data is collected using a probe, such as the probe 7 of FIG. 1, as scan lines. The image processing can be performed on a per scan line basis in one embodiment or a plurality of scan lines. In one embodiment, the intravascular data can be generated from scan lines and as such can be in the form of image frames.

Figure 7:
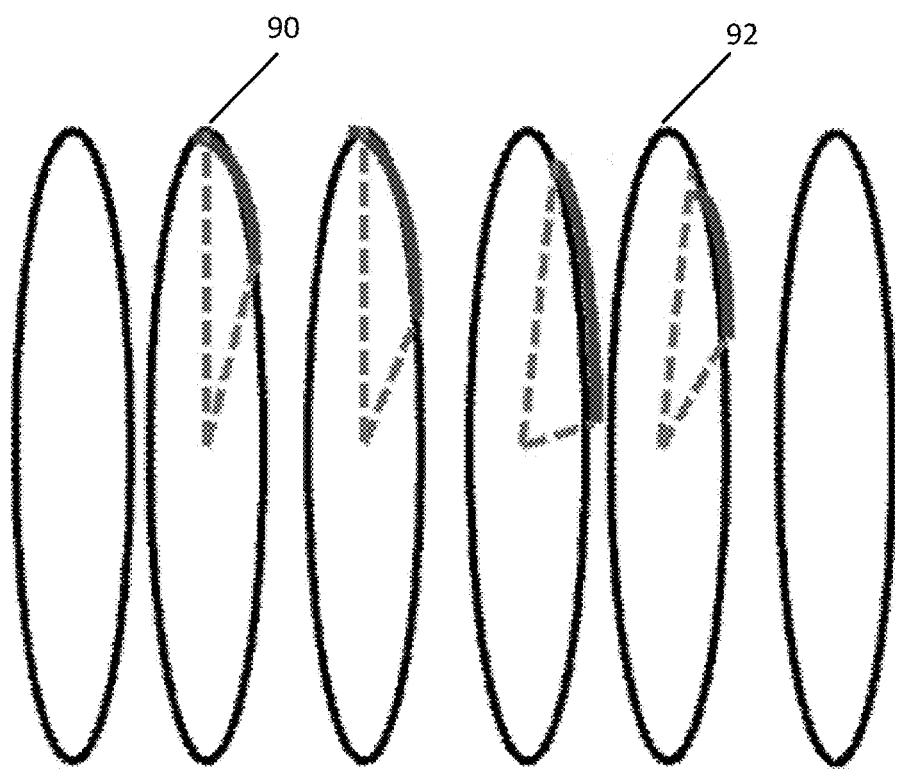
FIG. 7 is a schematic illustrating a subset of frames including a side branch opening with an illustrative embodiment of the disclosure.

In step 72, an algorithm is used to determine image frame subsets that include a side branch off the main vessel. A subset of frames can be identified for each side branch. An example of a subset of frame identified as illustrating a side branch of the main vessel is shown in FIG. 7. A branch start frame 90 is identified as a first frame to include a particular side branch opening from a main vessel. Subsequent frames are identified as including the same side branch opening until a branch end frame 92 is detected.

Figure 8:
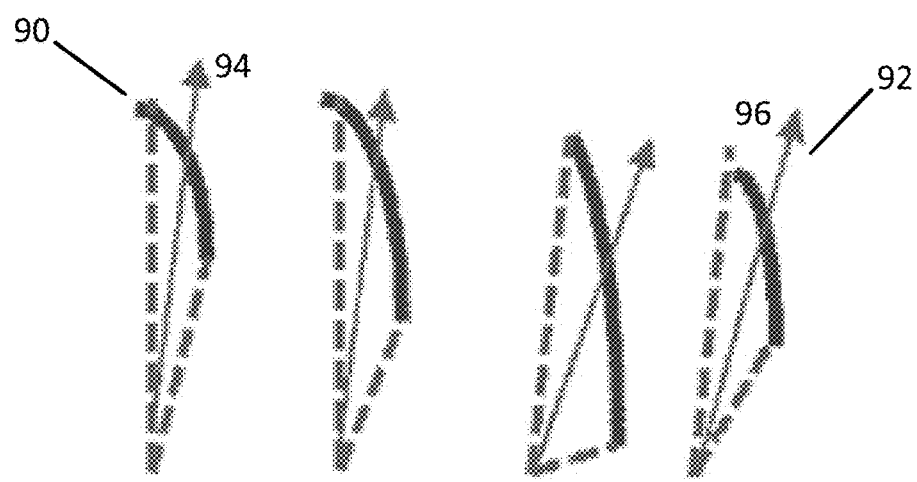
FIG. 8 is a schematic illustrating side branch opening angle calculations with an illustrative embodiment of the disclosure.

In step 74, a midpoint angle of the side branch opening is determined for a frame of the subset, and in step 76, this midpoint angle is stored in a database. As illustrated in FIG. 8, a midpoint angle 94 is calculated for the side branch opening detected in frame 90. A midpoint angle for the side branch opening is found for each frame in the subset, including a midpoint angle 96 for the branch end frame 92.

Figure 9:
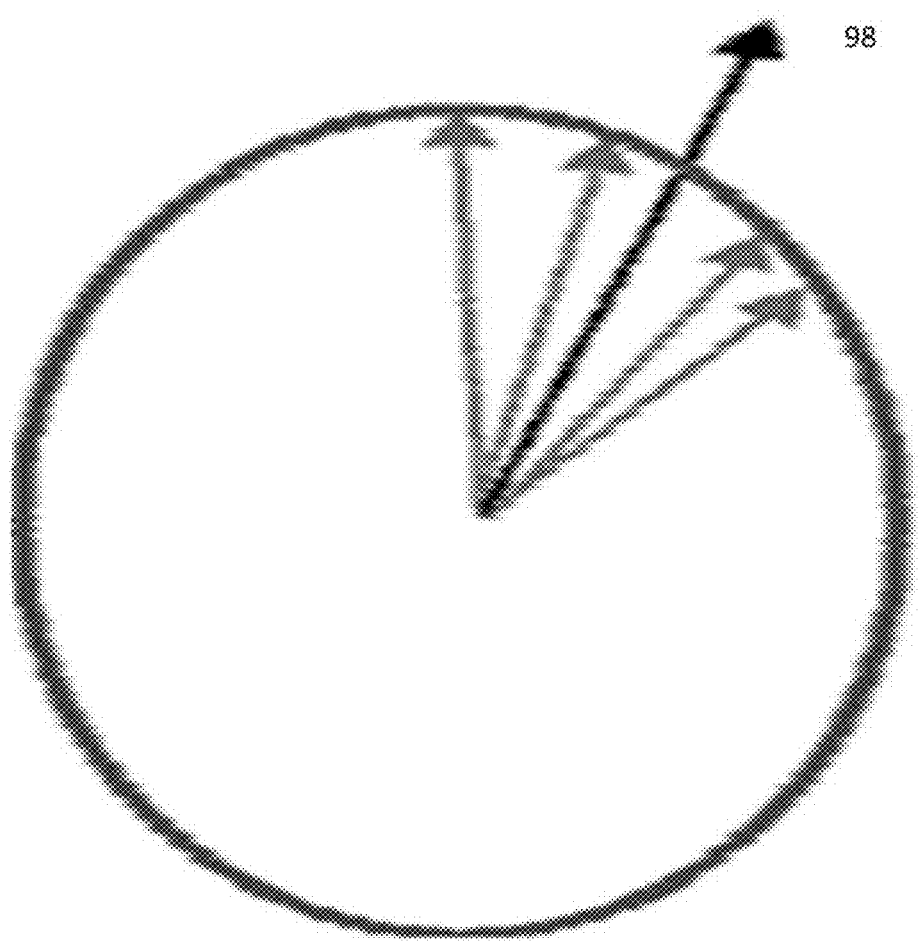
FIG. 9 is a schematic illustrating a side branch opening median angle determination in accordance with an illustrative embodiment of the disclosure.

In step 78, a determination is made as to whether or not there are more image frames in a subset. If there are additional frames, the midpoint angle is calculated for each additional frame and stored in the database, as explained above. If all the frames in the subset have been processed, a median angle for the midpoint angles from the subset of frames is calculated in step 80. FIG. 9 illustrates a median angle for the side branch opening as calculated using the midpoint angles for all the frames in a subset of frames including a particular side branch opening.

In step 82, the calculated median angle is used as the angle for a cut plane for visualization of a region of a side branch, for example, for carina detection. This method is performed for each subset of frames for each side branch detected from the set of image frames collected by the probe. Thus, the cut plane that is calculated for each side branch is one that is optimal for viewing each particular side branch to detect the presence of a carina. The determined cut planes can automatically be displayed to a user when a carina view mode is selected by the user or such as view made can be set as a default for a particular diagnostic application.

In another embodiment, the plane for visualizing the region of a side branch is determined by fitting a cylinder through an opening into the side branch. The axis of the side branch is estimated using the central axis of the cylinder. This axis can be used to determine an optical cut plane for visualizing a region of the side branch, and in particular for visualizing a carina of the side branch.

In part, the disclosure also relates to stent planning and optimization related software suitable for being used in the context of a pullback of a probe through an artery and the associated collected intravascular data. These software tools and the other methods and systems described herein is suitable for various research, diagnostic and applicable clinical actions such us to simulate, model or guide decisions relating to percutaneous coronary intervention (PCI). The methods and systems described herein are suitable for supporting PCI as a diagnostic tool in the pre-stenting phase and the post-stenting phase. One or more pullbacks of a probe before and after stenting may be performed to assess an artery, its side branches and associated bifurcations and carinas. The methods of carina visualization described herein can be used to support various research and diagnostic applications.

In part, in one embodiment, various automated measurements such as minimum lumen area determination and display in one or more panels of the user interface, lumen lengths and corresponding positions in angiography images displayed in the user interface, and other positions and fiducial references such as cut plane locations can be automatically displayed as a default setting. Alternatively, such information can be displayed selectively based on a user selecting each display option of interest. In one embodiment, automated measurements are toggled to on as the standard default for a lumen profile view of an artery.

In part, in one embodiment, as part of stent planning or deployed stent analysis a stent roadmap or other suitable stent user interfaces are available for display to the user such as those shown in FIGS. 4-5B.

In one embodiment, as described herein with regard to carina and side branch views, the disclosure includes a 3D Bifurcation Mode as a software feature by which bifurcations can be jumped to or toggled on and off along a longitudinal, cross-sectional, or other angled or 3D of an artery. Thus, a user can select a bifurcation mode or have it on automatically as a default for complex scenarios. The various angled viewing planes and associated display features of a bifurcation/carina view as shown in FIGS. 4 and 5A and 5B and other rotated or user configured displayed views of the bifurcation can be implemented using the systems, such as the system of FIG. 1 and the various software related methods and image processing steps described herein. The carina view can be turned on and off using the toggle 60 as shown in FIGS. 4 and 5A and 5B. The three-dimensional bifurcation mode uses side branch detection and a carina view to support diagnostic objectives of the end user.

Non-Limiting Software Features and Embodiments for Implementing Angiography and Intravascular Data Collection Methods and Systems The following description is intended to provide an overview of device hardware and other operating components suitable for performing the methods of the disclosure described herein. This description is not intended to limit the applicable environments or the scope of the disclosure. Similarly, the hardware and other operating components may be suitable as part of the apparatuses described above. The disclosure can be practiced with other system configurations, including personal computers, multiprocessor systems, microprocessor-based or programmable electronic devices, network PCs, minicomputers, mainframe computers, and the like.

Some portions of the detailed description are presented in terms of algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as "processing" or "computing" or "angling" or "selecting" or "toggling" or "calculating" or "comparing" or "arc length measuring" or "detecting" or "tracing" or "masking" or "sampling" or "operating" or "generating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present disclosure, in some embodiments, also relates to the apparatus for performing the operations herein. This apparatus may be specially constructed for the required purposes, or it may comprise a general purpose computer selectively activated or reconfigured by a computer program stored in the computer.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below.

Embodiments of the disclosure may be implemented in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof. In a typical embodiment of the present disclosure, some or all of the processing of the data collected using an OCT probe, an FFR probe, an angiography system, and other imaging and subject monitoring devices and the processor-based system is implemented as a set of computer program instructions that is converted into a computer executable form, stored as such in a computer readable medium, and executed by a microprocessor under the control of an operating system. Thus, user interface instructions and triggers based upon the completion of a pullback or a co-registration request, for example, are transformed into processor understandable instructions suitable for generating OCT data, changing viewing angle, toggling carina views between an on and off state, performing image procession using various and other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the internet or World Wide Web).

Various examples of suitable processing modules are discussed below in more detail. As used herein a module refers to software, hardware, or firmware suitable for performing a specific data processing or data transmission task. In one embodiment, a module refers to a software routine, program, or other memory resident application suitable for receiving, transforming, routing and processing instructions, or various types of data such as user interface control signals, image data, scan lines, image frames, OCT data, FFR data, IVUS data, pixels, viewing plane angles and orientation and coordinates, mean, median, mode, weighted average, average, user interface display features and various graphical display elements and other information of interest as described herein.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the disclosure described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the disclosure.

The aspects, embodiments, features, and examples of the disclosure are to be considered illustrative in all respects and are not intended to limit the disclosure, the scope of which is defined only by the claims. Other embodiments, modifications, and usages will be apparent to those skilled in the art without departing from the spirit and scope of the claimed disclosure.

The use of headings and sections in the application is not meant to limit the disclosure; each section can apply to any aspect, embodiment, or feature of the disclosure.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously.

It should be appreciated that various aspects of the claimed disclosure are directed to subsets and substeps of the techniques disclosed herein. Further, the terms and expressions employed herein are used as terms of description and not of limitation, and there is no intention, in the use of such terms and expressions, of excluding any equivalents of the features shown and described or portions thereof, but it is recognized that various modifications are possible within the scope of the disclosure claimed. Accordingly, what is desired to be secured by Letters Patent is the disclosure as defined and differentiated in the following claims, including all equivalents.

The term "machine-readable medium" includes any medium that is capable of storing, encoding or carrying a set of instructions for execution by the machine and that cause the machine to perform any one or more of the methodologies of the present disclosure. While the machine-readable medium is shown in an example embodiment to be a single medium, the term "machine-readable medium" should be taken to include a single medium or multiple media (e.g., a database, one or more centralized or distributed databases and/or associated caches and servers) that store the one or more sets of instructions.

It can be appreciated that, in certain aspects of the disclosure, a single component may be replaced by multiple components, and multiple components may be replaced by a single component, to provide an element or structure or to perform a given function or functions. Except where such substitution would not be operative to practice certain embodiments of the disclosure, such substitution is considered within the scope of the disclosure.

The examples presented herein are intended to illustrate potential and specific implementations of the disclosure. It can be appreciated that the examples are intended primarily for purposes of illustration of the disclosure for those skilled in the art. There may be variations to these diagrams or the operations described herein without departing from the spirit of the disclosure. For instance, in certain cases, method steps or operations may be performed or executed in differing order, or operations may be added, deleted or modified.

Furthermore, whereas particular embodiments of the disclosure have been described herein for the purpose of illustrating the disclosure and not for the purpose of limiting the same, it will be appreciated by those of ordinary skill in the art that numerous variations of the details, materials and arrangement of elements, steps, structures, and/or parts may be made within the principle and scope of the disclosure without departing from the disclosure as described in the claims.

What is claimed is:

1. A method of detecting a region of a side branch of a blood vessel comprising:
   identifying, using an imaging system, a subset of image frames that include a side branch of a blood vessel from a set of image frames, the image frames generated using data collected with regard to the blood vessel using the imaging system;
   calculating, using one or more software modules of the imaging system, a midpoint angle of a side branch opening in each frame of the subset of image frames;
   calculating, using the one or more software modules of the imaging system, a median angle of the side branch opening using the midpoint angles calculated for each frame of the subset of image frames;
   determining, using the one or more software modules of the imaging system, a visualization plane for viewing the side branch using the calculated median angle to allow for detection of a region associated with the side branch; and
   automatically display a portion of the side branch oriented based on the visualization plane in response to a user selection of a user interface control.

2. The method of claim 1, wherein the detected region associated with the side branch includes a carina.

3. The method of claim 2 further comprising generating, using the imaging system, a control signal to select a carina view in response to a user action.

4. The method of claim 1 further comprising displaying, using the one or more software modules of the imaging system, the region oriented relative to the viewing plane.

5. The method of claim 4 wherein the region comprises a carina.

6. The method of claim 5 further comprising generating, using the imaging system, a control signal to select a carina view in response to a user action.

7. The method of claim 1 further comprising automatically orienting a user view of the region in a cross-sectional viewing mode of a user interface.

8. The method of claim 1 further comprising automatically orienting a user view of the region in a three dimensional viewing mode of a user interface.

9. The method of claim 1 further comprising automatically orienting a user view of the region in response to activation of a user interface toggle.

10. The method of claim 1 wherein the imaging system is selected from the group consisting of an optical coherence tomography system, an intravascular ultrasound system, and an angiography system.

11. A system for detecting a region associated with a side branch of a vessel comprising:
    an imaging system comprising a processor, the processor executing one or more image detection software modules, wherein the one or more image detection modules are configured to process a plurality of images frames obtained from an optical coherence tomography pullback with respect to a blood vessel using an imaging probe,
    the one or more image detection software modules configured to
      process the plurality of image frames to detect one or more side branches of the blood vessel and
      calculate an angle of an opening of the side branch for each image frame in which a side branch is detected;
      determine a median angle for the opening of each side branch detected in the image frames;
    one or more memory devices configured to store the calculated angles of an opening of each side branch and the median angles,
    wherein the median angle for each side branch is used to determine a visualization plane for each side branch; and
    a display in communication with the processor, wherein the display outputs a view of a region of the side branch oriented using the visualization plane, wherein the display of the detected region of the side branch may be toggled on or off using the user interface.

12. The system of claim 11, wherein the detected region of the side branch includes a carina.

13. The system of claim 11, wherein the detected region of the side branch includes a stent portion and a side branch portion.

14. A method of detecting a region of a side branch of a blood vessel comprising:
    accessing a set of intravascular data stored in machine readable memory;
    performing side branch detection, using an imaging system executing one or more image detection software modules, with regard to the intravascular data to identify one or more side branches;

identifying, using the imaging system, a plurality of frames for the one or more identified side branches;

determining, using the imaging system, a consistent reference angle value for each of the plurality of frames;

statistically analyzing, using the imaging system, the plurality of consistent references angles using a statistical measure applied to the plurality of consistent reference angles; and selecting, using the imaging system, an overall statistically analyzed angle as a cut plane viewing angle;

automatically orienting a user view in response to activation of a user interface toggle using one or more selected cut plane view angles for a representation of the blood vessel generated on a display.

15. The method of claim 14 further comprising moving, using user interface control or toggle, to a carina or between two or more carinas detected using one or more image detection software modules.

16. The method of claim 14 automatically generating visualizations of one or more carinas in coronary bifurcations that are viewable using the overall statistically analyzed angle.

17. The method of claim 14 wherein the statistical measure is selected from the group consisting of a mean, a median, a mode, and a weighted average and a histogram.

18. The method of claim 14 wherein the overall statistically analyzed angle is a median angle for a plurality of midpoint angles.

19. The method of claim 14 further comprising controlling an "on" and "off" state of automatic display using the overall statistically analyzed angle via a user interface feature on a display of the representation of the intravascular data.

20. The method of claim 14 wherein the imaging system is selected from the group consisting of an optical coherence tomography system, an intravascular ultrasound system, and an angiography system.

* * * * *